United States Patent [19]

Krebs et al.

[11] Patent Number: 4,777,283

[45] Date of Patent: Oct. 11, 1988

[54] PROCESS FOR THE PREPARATION OF ALKOXYCARBONYL ISOCYANATES

[75] Inventors: Andreas Krebs, Odenthal-Holz; Hermann Hagemann, Leverkusen, both of Fed. Rep. of Germany

[73] Assignee: Bayer Aktiengesellschaft, Leverkusen, Fed. Rep. of Germany

[21] Appl. No.: 948,215

[22] Filed: Dec. 31, 1986

[30] Foreign Application Priority Data

Jan. 18, 1986 [DE] Fed. Rep. of Germany ....... 3601376

[51] Int. Cl.⁴ .............................................. C07C 69/00
[52] U.S. Cl. ...................................... 560/129; 560/347
[58] Field of Search ..................... 560/347, 129, 132

[56] References Cited

U.S. PATENT DOCUMENTS 3,492,331  1/1970  Sayigh et al. ...................... 560/347
3,746,746  7/1973  Pagano ............................... 560/129

FOREIGN PATENT DOCUMENTS 49-14206  4/1974  Japan ................................. 560/129

OTHER PUBLICATIONS

Ulrich et al., Angew Chem. Intemat. Ed. 6, 636–637 (1967).

Primary Examiner—Alan Siegel
Attorney, Agent, or Firm—Sprung Horn Kramer & Woods

[57] ABSTRACT

Alkoxycarbonyl isocyanates are prepared from carbamic acid esters by reacting these with phosgene and adding a catalyst.

9 Claims, No Drawings

PROCESS FOR THE PREPARATION OF ALKOXYCARBONYL ISOCYANATES

The present invention relates to a process for the preparation of alkoxycarbonyl isocyanates from N-unsubstituted carbamic acid esters or ureadicarboxylic acid esters.

It is already known that ethoxycarbonyl isocyanates can be obtained by reaction of triethyl nitrogentricarboxylates with phosphorus pentoxide (O. Diels and B. Wolf. Ber. Dtsch. Chem. Ges. 39, 688 (1906)). Alkoxycarbonyl isocyanates can also be obtained from N-unsubstituted carbamic acid esters and oxalyl chloride, from alkoxycarbonyl-isocyanide dichlorides and methanesulphonic acid, and from alcohols and chlorocarbonyl isocyanate or N-chlorocarbonyl-iminocarbonyl chloride esters (see H. Hagemann in Houben-Weyl, volume E4, page 1238 (1983)). Common to all these processes is that they require at least one reactant which is accessible, in industrial amounts, only with difficulty or not at all.

It is furthermore known that ureadicarboxylic acid esters are produced on phosgenation of N-unsubstituted carbamic acid esters (see A. Botta in Houben-Weyl, ibid., page 1321).

A process for the preparation of alkoxycarbonyl isocyanates from carbamic acid esters has now been found which is characterized in that carbamic acid esters of the formula

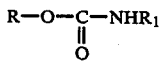     (I)

in which
R represents an optionally substituted alkyl, cycloalkyl or aralkyl radical and
$R_1$ represents hydrogen or

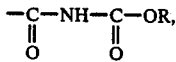

where R has the abovementioned meaning,
are reacted with phosgene and a catalyst is added.

In formula (I), R can represent, for example, an alkyl radical having 1 to 20 C atoms, a cycloalkyl radical having 4 to 20 C atoms or an aralkyl radical having 7 to 20 C atoms. All these radicals can be substituted, for example by one or more $C_1$–$C_{10}$-alkyl radicals, one or more halogen atoms or one or more $C_1$–$C_{10}$-alkoxy groups. Of the halogen atoms, fluorine, chlorine and bromine are preferred here. The radical R in formula (I) is preferably a straight-chain or branched alkyl group which is optionally substituted by fluorine, chlorine or a $C_1$–$C_5$-alkoxy group and contains a total of 1 to 10 C atoms, a cycloalkyl group which is optionally substituted by $C_1$–$C_5$-alkyl, fluorine, chlorine or $C_1$–$C_5$-alkoxy and contains a total of 5 to 12 C atoms, or an aralkyl radical which is optionally substituted by $C_1$–$C_5$-alkyl, fluorine, chlorine or $C_1$–$C_5$-alkoxy and contains a total of 7 to 12 C atoms. Examples of R are methyl, ethyl, n-propyl, isopropyl, n-butyl, isobutyl, sec.-butyl, n-pentyl, 3-methylbutyl, 2,2-dimethylpropyl, n-hexyl, 1,3-dimethylbutyl, 2-ethylbutyl, 2-ethylhexyl, nonyl, decyl, dodecyl, tetradecyl, hexadecyl, octadecyl, cyclohexyl, cyclohexylmethyl, 4-tert.-butylcyclohexyl, menthyl, benzyl, phenylethyl, 2-methoxyethyl, 2-ethoxyethyl, 2-propoxyethyl, 2-butoxyethyl, 2-(2-ethoxyethoxy)-ethyl, 2-chloroethyl, 4-chlorobutyl, 2,2,2-trichloroethyl and 2,2,2-trifluoroethyl.

When $R_1$ in formula (I) represents

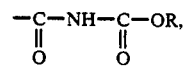

the compounds of the formula (I) are ureadicarboxylic acid esters. These do not necessarily have to contain the same radicals R in both parts, but this is preferable. The meaning $R_1$=hydrogen is preferred of the two meanings of $R_1$.

Phosgene can be employed in the process according to the invention for example in gaseous form or liquefied under pressure and in customary purities. Starting from carbamic acid esters of the formula (I) with $R_1$=hydrogen, at least 1 mole of phosgene is preferably employed per mole of carbamic acid ester for the reaction according to the invention, and starting from carbamic acid esters of the formula (I) with $R_1$=

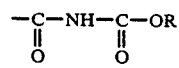

Likewise at least 1 mole of phosgene is preferably employed per mole of carbamic acid ester. The phosgene can be employed in any excesses desired in the process according to the invention. For economic reasons. no more than 10 moles of phosgene are in general employed per mole of carbamic acid ester, or unreacted phosgene is recycled, for example by passing the gas outlet stream through a reflux condenser which is cooled to below the condensation point of phosgene.

Examples of suitable catalysts for the process according to the invention are N-disubstituted formamides. These can contain, on the nitrogen atom, two identical or different substituents which can be, for example, straight-chain or branched alkyl groups having a total of 1–20 C atoms, but also cycloalkyl groups having 4 to 12 C atoms, aralkyl groups having 7 to 12 C atoms and/or aryl groups having 6 to 12 C atoms. All these groups can themselves be optionally substituted. The alkyl groups can be optionally substituted by fluorine, chlorine and/or $C_6$–$C_{10}$-aryl, the cycloalkyl groups can be optionally substituted by fluorine, chlorine, $C_1$–$C_{10}$-alkyl and/or $C_6$–$C_{10}$-aryl, the aralkyl groups can be optionally substituted by fluorine, chlorine, $C_1$–$C_{10}$-alkyl (in the aryl part) or $C_6$–$C_{10}$-aryl (in the alkyl part) and the aryl groups can be optionally substituted by fluorine, chlorine, $C_1$–$C_{10}$-alkyl or $C_4$–$C_8$-cycloalkyl.

Examples of suitable catalysts for the process according to the invention are also those N-disubstituted formamides in which the nitrogen atom is a component of the heterocyclic ring system, for example of a pyrrolidine, piperidine or morpholine ring system.

Examples of catalysts which may be mentioned are: N,N-dimethylformamide, N,N-diethylformamide, N,N-di-(n)-propylformamide, N,N-isopropylformamide, N,N-di-(n)-butylformamide, N,N-di-sec.-butylformamide, N,N-diisobutylformamide, N,N-di-(n)-hexylformamide, N,N-di-(2-ethylhexyl)formamide, N,N-didodecylformamide, N-butyl-N-ethylformamide, N-methyl-N-stearylformamide, N-cyclohexyl-N-methylformamide, N,N-dicyclohexylformamide, N-metylformanilide, N-butylformanilide, N,N-dibenzylformamide, N-formylpyrrolidine, N-formylpiperidine and N-formylmorpholine.

Bifunctional formamides, for example, N,N'-dimethyl-N,N'-diformyl-ethylenediamine, can also be employed as catalysts.

The amount of catalyst is, in general, not critical. Suitable applicational amounts are, for example, 0.02 to 50 mol % of catalyst, relative to the compound of the formula (I) employed. This amount is preferably 0.2 to 5 mol %.

The addition of the catalyst can occur at various points in time. For example, the catalyst can be added at the beginning, that is to say before the phosgene is added. It is frequently possible, without having to accept any disadvantages, not to add the catalyst until the reaction is underway, particularly when starting from compounds of the formula (I) in which $R_1$ represents hydrogen.

The process according to the invention can be carried out in the presence or absence of solvents. The presence of solvents is frequently advantageous, particularly in order to have a good heat transfer and/or an easily stirrable batch. Suitable solvents are those which are virtually or completely inert under the reaction conditions. Suitable are, for example, aliphatic hydrocarbons, preferably those with boiling points between 80 and 300° C., such as heptane, octane, methylcyclohexane, ligroin and petroleum ether, aromatic hydrocarbons such as toluene, xylene, isopropylbenzene, 1-methylnaphthalene and biphenyl, halogenated aliphatic hydrocarbons such as tetrachloromethane, 1,2-dichloroethane, 1,1,1-trichloroethane and 1,1,2,2-tetrachloroethane, halogenated aromatic hydrocarbons such as chlorobenzene, 1,2-dichlorobenzene, 1,2,4-trichlorobenzene and 1-chloronaphthalene, and also esters such as ethyl acetate, butyl acetate, 2-ethylhexyl acetate, 1,2-diacetoxyethane, ethyl benzoate and diethyl carbonate. Particularly preferred solvents are chlorobenzene and 1,2-dichlorobenzene. If solvents are employed, these can be employed, for example, in amounts from 10 to 1000% by weight, relative to the carbalic acid ester of the formula (I).

The process according to the invention can be carried out, for example, at temperatures from 20° to 200° C. The reaction temperature is preferably 60° to 180° C. The reaction can be carried out at atmospheric pressure, increased pressure and reduced pressure. The reaction is preferably carried out at atmospheric pressure or slightly increased pressure, for example at 1 to 5 bar. The carbamic acid ester of the formula (I) can be reacted according to the invention with phosgene not only in the form of a solution in one of the abovementioned solvents, but also in melted form, in which case the catalyst and, if appropriate, a solvent can also be added at a later point in time, that is to say after the first addition of phosgene.

The reaction mixture present after the reaction according to the invention can be worked up, for example, by fractional distillation at atmospheric or reduced pressure. The solvent possibly recovered during the workup can be used for further batches. After the separation of readily volatile components of the reaction mixture and of the alkoxycarbonyl isocyanate prepared, a residue generally remains which can contain the catalyst employed and compounds, which can be converted to alkoxycarbonyl isocyanates under the reaction conditions to be used according to the invention. It is therefore advantageous, in general, to add such a residue, completely or partially, if appropriate with addition of fresh catalyst, to a further batch for carrying out the process according to the invention.

Compared to the known reaction of carbamic acid esters with oxalyl chloride, the process according to the invention offers the advantage that hydrogen chloride is produced as the only gaseous reaction product, whereas a mixture of carbon monoxide and hydrogen chloride is produced during the reaction with oxalyl chloride. In addition, starting substances are required for the process according to the invention which are also easily accessible in industrial amounts.

It is extremely surprising that alkoxycarbonyl isocyanates can be so well prepared by the process according to the invention, since only the formation of ureadicarboxylic acid esters could have been expected according to A. Botta in Houben-Weyl, ibid.

The compounds which can be obtained by the process according to the invention are known alkoxycarbonyl isocyanates, which can be used, for example, as valuable intermediates in organic chemistry, or also as stabilizers for polyurethanes containing free isocyanate groups (see DE-OS (German Published Specification) No. 2,539,728).

EXAMPLES

Example 1

86.5 g of 2-ethylhexyl carbamate were initially introduced in melted form and 81 g of phosgene were passed into the melt at 80° C. within 6 hours. 250 g of chlorobenzene and 3.1 g (=2 mol %) of methylstearylformamide were then added, heated to 130° C. while a further 108 g of phosgene were passed into the mixture, and stirred for 6 hours under reflux cooling. Excess phosgene was subsequently blown out at 130° C. using nitrogen. The mixture was subsequently distilled through a 40 cm long Vigreux column, 74.7 g (=75% of theory) of 2-ethylhexyloxycarbonyl isocyanate having a boiling point of 62° to 66° C. at 0.8 mbar being obtained.

EXAMPLE 2

The procedure as in Example 1 was carried out, but 3.1 g (=4 mol %) of di-n-butylformamide were used as catalyst. 70.7 g (=71% of theory) of 2-ethylhexyloxycarbonyl isocyanate having a boiling point of 42° to 46° C. at 0.07 mbar were obtained.

EXAMPE 3

The procedure as in Example 1 was carried out, but 250 g of butyl acetate were employed instead of chlorobenzene. 59.4 g (=60% of theory) of 2-ethylhexyloxycarbonyl isocyanate having a boiling point of 68° to 70° C. at 0.9 mbar were obtained.

EXAMPLE 4

58.5 g of n-butyl carbamate were initially introduced as a melt and 86 g of phosgene were passed into this melt at 80° C. within 6 hours. 3.1 g (=2 mol %) of methylstearylformamide and 125 g of chlorobenzene were then added. A further 113 g of phosgene were then passed into the mixture at 130° C. within 6 hours and excess phosgene was subsequently blown out using nitrogen. The distillation of the reaction mixture produced 32.2 g (=45% of theory) of butyloxycarbonyl isocyanate having a boiling point from 52° to 54° C. at 24 mbar.

EXAMPLE 5

45 5 g of δ-chlorobutyl carbamate were initially introduced as a melt and 63 g of phosgene were passed into the melt at 80° C. within 6 hours. 150 g of chlorobenzene and 0.36 g (=0.4 mol %) of methylstearylformamide were then added and a further 159 g of phosgene were passed into the mixture at 130° C. over a further 16 hours. Excess phosgene was subsequently driven out using nitrogen. 23.7 g of δ-chlorobutyloxycarbonyl isocyanate having a boiling point of 86° to 109° C. at 20 mbar were obtained on subsequent distillation, corresponding to a yield of 44% of theory.

EXAMPLE 6

35.7 g of 2-methoxyethyl carbamate were phosgenated analogously to Example 5 to form 2-methoxyethyloxycarbonyl isocyanate. The boiling point of the product was 71° to 74° C. at 20 mbar, the yield was 12.9 g (=30% of theory).

EXAMPLE 7

18.0 g of diethyl ureadicarboxylate were initially introduced into 50 g of 1,2-dichlorobenzene, 1.3 g of methylstearylformamide were added, and a total of 52 g of phosgene were passed into the mixture over 3 hours at 130° C. and 2 hours at 180° C., the product being simultaneously removed by distillation. 6.9 g (30% of theory) of ethoxycarbonyl isocyanate having a boiling point of 25° to 35° C. at 14 mbar were obtained on further distillation of the crude product.

EXAMPLE 8

138.6 g of 2-ethylhexyl carbamate were initially introduced in melted form and 93 g of phosgene were passed into the melt at 80° C. within 3.25 hours, the gas outlet stream being passed through a reflux condenser cooled to −78° C. 800 g of chlorobenzene and 5.0 g of methylstearylformamide were then added, the mixture was heaLed to 120° C., and 48 g of phosgene were passed into the mixture within 3 hours. The mixture was stirred for a further 1 hour at 130° C. and excess phosgene was subsequently blown out using nitrogen. Subsequent distillation produced 135.5 g (=85% of theory) of 2-ethylhexyloxycarbonyl isocyanate having a boiling point of 45°–60° C. at 0.13–0.4 mbar.

What is claimed is:

1. A process for the preparation of an alkoxycarbonyl isocyanate from a carbamic acid ester, wherein a carbamic acid ester of the formula

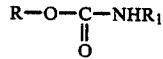

in which

R represents an unsubstituted or substituted alkyl, cycloalkyl or aralkyl radical and $R_1$ represents hydrogen or

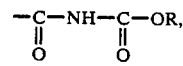

where
R has the abovementioned meaning, is reacted with phosgene and a catalyst is added where said catalyst is a N-disubstituted formamide.

2. A process according to claim 1, wherein R represents an unsubstituted or substituted alkyl radical having 1 to 20 C atoms, cycloalkyl radical having 4 to 20 C atoms or aralkyl radical having 7 to 20 C atoms.

3. A process according to claim 1, wherein the substituents on the radical R are selected from $C_1$–$C_{10}$-alkyl radicals, halogen, and $C_1$–$C_{10}$-alkoxy group.

4. A process according to claim 1, wherein $R_1$ represents hydrogen.

5. A process according to claim 1, wherein at least 1 mole of phosgene is employed per mole of carbamic acid ester in the case where $R_1$=hydrogen and at least one mole of phosgene is employed per mole of carbamic acid ester in the case where $R_1$=

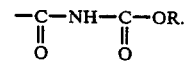

6. A process according to claim 1, wherein the N-disubstituted formamide contains straight-chain or branched alkyl groups having 1 to 20 C atoms, cycloalky groups having 4 to 12 C atoms, aralkyl groups having 7 to 12 C atoms and/or aryl having 6 to 12 C atoms as substituents which are themselves optionally substituted.

7. A process according to claim 1 wherein the N-disubstituted formamide is N,N-dimethylformamide, N,N-diethylformamide, N,N-di-(n)-propylformamide, N,N-isopropylformamide, N,N-di-(n)-butylformamide, N,N-di-sec.-butylformamide, N,N-diisobutylformamide, N,N-di-(n)-hexylformamide, N,N-di-(2-ethylhexyl)-formamide, N,N-didodecylformamide, N-butyl-N-ethylformamide, N-methyl-N-stearylformamide, N-cyclohexyl-N-methylformamide, N,N-dicyclohexylformamide, N-methylformanilide, N-butylformanilide, N,N-dibenzylformamide, N-formylpyrrolidine, N-formylmorpholine or N,N′-dimethyl-N,N′-diformylethylenediamine.

8. A process according to claim 1, wherein the catalyst is employed in an amount from 0.02 to 50 mol %, relative to the carbamic acid ester employed.

9. A process according to claim 1, wherein the reaction is carried out at temperature from 20° to 200° C.

* * * * *

UNITED STATES PATENT AND TRADEMARK OFFICE
CERTIFICATE OF CORRECTION

PATENT NO. : 4,777,283

DATED : Oct. 11, 1988

INVENTOR(S) : Krebs et al.

It is certified that error appears in the above-identified patent and that said Letters Patent is hereby corrected as shown below:

| | |
|---|---|
| Col. 2, line 68 | Correct spelling of --N-methylformanilide-- |
| Col. 3, line 42 | Correct spelling of --carbamic-- |
| Col. 5, line 3 | Insert --.-- after "45" |
| Col. 5, line 41 | Correct spelling of --heated-- |
| Col. 6, line 49 | Insert --N-formylpiperidine-- after "N-formylpyrrolidine" |

Signed and Sealed this

Eighth Day of August, 1989

Attest:

DONALD J. QUIGG

*Attesting Officer*    *Commissioner of Patents and Trademarks*